US00PP07983P

United States Patent [19]

Stravers

[11] Patent Number: Plant 7,983

[45] Date of Patent: Sep. 22, 1992

[54] GERBERA PLANT NAMED TERKAPOL

[75] Inventor: Lambertus J. M. Stravers, Kudelstaart, Netherlands

[73] Assignee: Terra Nigra BV, PA De Kwakel, Netherlands

[21] Appl. No.: 645,601

[22] Filed: Jan. 25, 1991

[51] Int. Cl.[5] ..... A01H 5/00
[52] U.S. Cl. ..... Plt./68.1
[58] Field of Search ..... Plt./68

*Primary Examiner*—James R. Feyrer
*Attorney, Agent, or Firm*—Foley & Lardner

[57] ABSTRACT

A new and distinct cultivar of Gerbera plant named Terkapol, characterized by its duplex/triplex type and flat flower form, bright yellow outer ray florets, yellow perianth lobes, dark purple disc center, and total flower diameter of 60–69 mm.

1 Drawing Sheet

The present invention comprises a new and distinct cultivar of Gerbera, botanically known as *Gerbera jamesonii,* and referred to by the cultivar name Terkapol.

Terkapol was originated from a hybridization made by the inventor in a controlled breeding program in De Kwakel, The Netherlands in 1988.

The female parent was a cultivar designated 87.442. The male parent was a cultivar designated M88.330. The new cultivar was discovered and selected as one flowering plant within the progeny of the stated parentage by applicant in January 1989 in a controlled environment in De Kwakel.

The first asexual reproduction of Terkapol was accomplished when vegetative cuttings were taken by applicant from the initial selection in April 1989 in a controlled environment in De Kwakel, The Netherlands. Horticultural examination of selected units initiated in November 1989 has demonstrated that the combination of characteristics as herein disclosed for Terkapol are firmly fixed and are retained through successive generations of asexual reproduction. The new cultivar is presently being propagated by cuttings and by tissue culture.

Terkapol has not been observed under all possible environmental conditions. The phenotype may vary significantly with variations in environment such as temperature, light intensity and day length. The following observations, measurements and comparisons describe plants grown in the greenhouse of Terra Nigra BV in De Kwakel, The Netherlands under controlled conditions which closely approximate those generally used in commercial practice.

The following traits have been repeatedly observed and have been determined to be basic characteristics of Terkapol, which in combination distinguish this Gerbera as a new and distinct cultivar:

1. Duplex/triplex flower type.
2. Flat flower form.
3. Bright yellow ray floret color.
4. Yellow perianth lobes.
5. Dark purple disc.

Of the many commercial cultivars known to the present inventor, there is none which can be meaningfully compared to Terkapol and its unique combination of characteristics.

The accompanying photograph drawing shows typical inflorescence characteristics of Terkapol, with the colors being as nearly true as possible with illutrations of this type. The photograph comprises a closeup view of the flower form and color of the new cultivar. The photograph is relatively dull and fails to capture the bright intense yellow ray floret color. The color values set forth below are correct.

In the following description, color references are made to The Royal Horticultural Society Colour Chart (R.H.S.). The color values were determined at approximately 12:00 noon on Nov. 9, 1990 under artificial light at De Kwakel, The Netherlands.

Classification:
- *Botanical.*—*Gerbera jamesonii* cv. Terkapol.
- *Commercial.*—Gerbera.

Parentage: Seedling from cross of 87.442 and M88.330.

Plant: The plant when fully grown reaches a height of 40 cm.

Leaf blade:
- *Length.*—Short, 40–45 cm.
- *Width.*—Narrow, 16 cm.
- *Thickness.*—Medium.
- *Blistering (puckering).*—Medium.
- *Pubescence on upper side.*—Sparse (midrib excluded).
- *Depth of cuts or incisions in leaf.*—Near bottom or base: Strong. Near middle: Medium. Near tip: Weak.
- *Color.*—Upper surface of leaf, medium green 137A; lower surface, light green.
- *Glossiness on upper side.*—Weak.
- *Angle of apex.*—Obtuse.
- *Shape of apex.*—Rounded.
- *Martin of lobes.*—Dentate.
- *Extension of margin.*—Absent.
- *Petiole length.*—Medium, 10 cm.
- *Petiole anthocyanin coloration.*—Present, medium in intensity.

Peduncle:
- *Length.*—Medium, 60 cm.
- *Cross section.*—Round, medium thick and strong.
- *Tendency to fasciation.*—Absent.
- *Pubescence.*—Medium.
- *Color.*—Medium green.
- *Anthocyanin.*—Present at base, medium in intensity, none present at tip.

*Bracts near tip.*—None.

Flower head:

*Type.*—Duplex/triplex. Single, with dark purple center; generally flat shaped in form.

*Diameter from edge to edge.*—60–69 mm.

*Height.*—From point of attachment of involucre to top of flower head is medium 22 cm.

*Involucre.*—Height: Medium, 16 mm. Diameter: Small, 27 mm. Number of bracts: 60; longitudinal axis of bracts of inner rows of involucre is straight. Anthocyanin: Present on top of inner bracts. Pubescence: Weak.

*Outer row of ray florets.*—Number in outer row: 40–60 Length of floret: Under 29 mm. Width of floret: 5–9 mm. Shape of floret: Longitudinal folding medium. Cross section of floret: Concave. Length of free petals: Under 29 mm. Color distribution on inner side: Uniform; edge is of same color. Striation: Absent. Claw spot: Present. Color on top side: 12A. Color on bottom side: 8B. Angle of apex: Obtuse. Shape of apex: Rounded. Incisions of apex: Present, one in number; shallow in depth.

*Disc florets.*—Diameter: 10–19 mm. Main color in perianth lobes: Yellow for both male and female flowers. Color (mature and immature): Dark purple.

Reproductive parts:

*Stigma.*—Main color, yellow.

*Anthers.*—Main color: Yellow; color at top lighter relative to other parts. Longitudinal striping: Present.

*Pappus.*—Main color: Brown; color at top is red relative to other parts. Orientation: Level of top is the same relative to closed disc florets.

I claim:

1. A new and distinct cultivar of Gerbera plant named Terkapol, as illustrated and described.

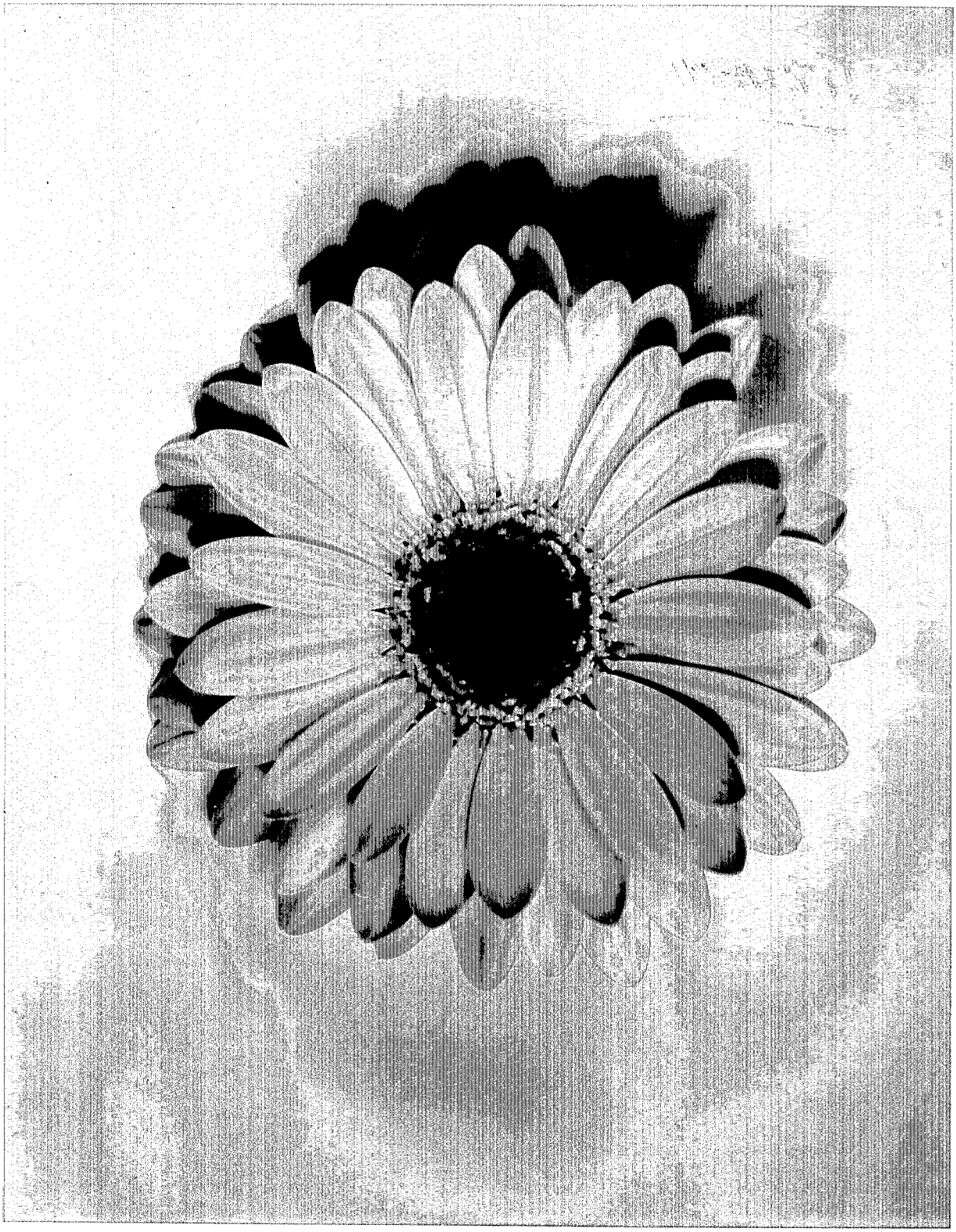

* * * * *